United States Patent [19]

Giddey et al.

[11] Patent Number: 5,310,540

[45] Date of Patent: May 10, 1994

[54] METHOD FOR THE PREPARATION OF STABLE SUSPENSIONS OF HOLLOW GAS-FILLED MICROSPHERES SUITABLE FOR ULTRASONIC ECHOGRAPHY

[75] Inventors: Claude Giddey, Geneva; Georges Dove, Carouge, both of Switzerland

[73] Assignee: Sintetica SA, Mendrisio, Switzerland

[21] Appl. No.: 855,032

[22] PCT Filed: Sep. 13, 1991

[86] PCT No.: PCT/EP91/01706
§ 371 Date: May 6, 1992
§ 102(e) Date: May 6, 1992

[87] PCT Pub. No.: WO92/05806
PCT Pub. Date: Apr. 16, 1992

[30] Foreign Application Priority Data

Oct. 5, 1990 [EP] European Pat. Off. ......... 90810768.3

[51] Int. Cl.⁵ .................. A61K 49/00; A61K 9/50
[52] U.S. Cl. ...................... 424/9; 128/660.01; 128/662.02; 424/450
[58] Field of Search ............... 424/9, 450; 128/662.02, 128/660.01

[56] References Cited

U.S. PATENT DOCUMENTS

| 4,466,442 | 8/1984 | Hilmann et al. | 128/653.1 |
| 4,957,656 | 9/1990 | Cerny et al. | 424/9 |
| 5,154,914 | 10/1992 | Elgavish et al. | 424/9 |

FOREIGN PATENT DOCUMENTS

| 77752 | 4/1983 | European Pat. Off. | 128/662.02 |
| 123235 | 10/1984 | European Pat. Off. | 424/9 |
| 131540 | 1/1985 | European Pat. Off. | 424/9 |
| 324938 | 7/1989 | European Pat. Off. | 424/9 |
| 359246 | 3/1990 | European Pat. Off. | 424/9 |

OTHER PUBLICATIONS

Z. B. Shafi et al., *Pharmacy and Pharmacology*, 42, Dec. 1990, British Pharmaceutical Conference, Science Proceedings 127th meeting Sep. 10-13, 1990.

*Primary Examiner*—Richard L. Raymond
*Attorney, Agent, or Firm*—Nixon & Vanderhye

[57] ABSTRACT

A viscous solution of a filmogenic protein is whipped into a foam and the foam is subjected to shear to reduce the size of the foam bubbles to a range (about 0.5–10 μm) suitable for echography. The proteins include animal and vegetal proteins or partial hydrolyzates thereof with foaming properties. The suspensions of microspheres can be stabilized by heat or by cross-linkers.

22 Claims, No Drawings

METHOD FOR THE PREPARATION OF STABLE SUSPENSIONS OF HOLLOW GAS-FILLED MICROSPHERES SUITABLE FOR ULTRASONIC ECHOGRAPHY

The present invention concerns a method for preparing stable dispersions or solutions of air or gas filled microspheres in aqueous liquids suitable for being injected into living beings, for instance for ultrasonic echography and other medical applications.

The invention also concerns compositions which may be subjected to the foregoing method as well as the desired stable microsphere solutions or suspensions which result from carrying out the method.

It is well known that microbodies or microglobules of air or a gas, e.g. microbubbles or microballoons, suspended in a liquid are exceptionally efficient ultrasound reflectors for echography. In this disclosure the term of "microbubble" specifically designates air or gas globules in suspension in a liquid which generally results from the introduction therein of air or a gas in divided form, the liquid preferably also containing surfactants or tensides to control the surface properties and the stability of the bubbles. The term of "microcapsule" or "microballoon" designates preferably air or gas bodies with a material boundary or envelope, i.e. a polymer membrane wall. Both microbubbles and microballoons are useful as ultrasonic contrast agents. For instance injecting into the blood-stream of living bodies suspensions of gas microbubbles or microballoons (in the range of 0.5 to 10 μm) in a carrier liquid will strongly reinforce ultrasonic echography imaging, thus aiding in the visualization of internal organs. Imaging of vessels and internal organs can strongly help in medical diagnosis, for instance for the detection of cardiovascular and other diseases.

The formation of suspensions of microbubbles in an injectable liquid carrier suitable for echography can be produced by the release of a gas dissolved under pressure in this liquid, or by a chemical reaction generating gaseous products, or by admixing with the liquid soluble or insoluble solids containing air or gas trapped or adsorbed therein.

For instance, in U.S. Pat. No. 4,446,442 (Schering), there are disclosed a series of different techniques for producing suspensions of gas microbubbles in a sterilized injectable liquid carrier using (a) a solution of a tenside (surfactant) in a carrier liquid (aqueous) and (b) a solution of a viscosity enhancer as stabilizer. For generating the bubbles, the techniques disclosed there include forcing at high velocity a mixture of (a), (b) and air through a small aperture; or injecting (a) into (b) shortly before use together with a physiologically acceptable gas; or adding an acid to (a) and a carbonate to (b), both components being mixed together just before use and the acid reacting with the carbonate to generate $CO_2$ bubbles; or adding an over-pressurized gas to a mixture of (a) and (b) under storage, said gas being released into microbubbles at the time when the mixture is used for injection.

EP-A-131 540 (Schering) discloses the preparation of microbubble suspensions in which a stabilized injectable carrier liquid, e.g. a physiological aqueous solution of salt, or a solution of a sugar like maltose, dextrose, lactose or galactose, is mixed with solid microparticles (in the 0.1 to 1 μm range) of the same sugars containing entrapped air. In order to develop the suspension of bubbles in the liquid carrier, both liquid and solid components are agitated together under sterile conditions for a few seconds and, once made, the suspension must then be used immediately, i.e. it should be injected within 5-10 minutes for echographic measurements; indeed, because they are evanescent, the bubble concentration becomes too low for being practical after that period. Hence, one critical problem related to the use of microbubble solutions for injection is lack of stability with time. The present invention proposes to remedy this drawback.

Another problem with microbubbles for echography after injection is size. As commonly admitted, microbubbles of useful size for allowing transfer through small blood vessels range from about 0.5 to 10 μm; with larger bubbles, there are risks of clots and consecutive embolism. For instance, in the bubble suspensions disclosed in U.S. Pat. No. 4,446,442 (Schering) in which aqueous solutions of surfactants such as lecithin, esters and ethers of fatty acids and fatty alcohols with polyoxyethylene and polyoxyethylated polyols like sorbitol, glycols and glycerol, cholesterol, or polyoxy-ethylene-polyoxypropylene polymers, are vigorously shaken with solutions of viscosity raising and stabilizing compounds such as mono- and polysaccharides (glucose, lactose, sucrose, dextran, sorbitol), polyols, e.g. glycerol, polyglycols; and polypeptides like proteins, gelatin, oxypolygelatin and plasma protein, only about 50% of the microbubbles are below 40-50 μm which makes such suspensions unsuitable in many echographic applications. The present invention also permits to settle this problem by mechanically reducing the size of the bubbles.

In an attempt to cure some of the foregoing deficiencies, particularly the evanescence problem, microballoons, i.e. microspheres with a material wall, have been developed. As said before, while the microbubbles only have an immaterial or evanescent envelope, i.e. they are only surrounded by a wall of liquid whose surface tension is being modified by the presence of a surfactant, the microballoons or microcapsules have a tangible envelope made of substantive material, e.g. a polymeric membrane with definite mechanical strength. In other terms, they are microspheres of material in which the air or gas is more or less tightly encapsulated.

For instance, U.S. Pat. No. 4,276,885 (Tickner et al.) discloses using surface membrane microcapsules containing a gas for enhancing ultrasonic images, the membrane including a multiplicity of non-toxic and non-antigenic organic molecules. In a disclosed embodiment, these microbubbles have a gelatin membrane which resists coalescence and their preferred size is 5-10 μm. The membrane of these microbubbles is said to be sufficiently stable for making echographic measurements; however it is also said that after a period of time the gas entrapped therein will dissolve in the blood-stream and the bubbles will gradually disappear, this being probably due to slow dissolution of the gelatin. Hence the instability problem is not completely cured by this technique and before use, the microcapsules are kept in gelatin solutions in which they are storage stable; but the gelatin needs to be heated and melted to become liquid at the time the suspension is used for making injection which is inconvenient.

Microspheres of improved storage stability although without gelatin are disclosed in U.S. Pat. No. 4,718,433 (Feinstein). These microspheres are made by sonication (5 to 30 KHz) of protein solutions like 5% serum albumin and have diameters in the 2-20 μm range, mainly 2-4 μm. The microspheres are stabilized by denaturation of the membrane forming protein after sonication, for instance by using heat or by chemical means, e.g. by reaction with formaldehyde or glutaraldehyde. The concentration of stable microspheres obtained by this technique is said to be about $8 \times 10^6$/ml in the 2-4 μm range, about $10^6$/ml in the 4-5 μm range and less than $5 \times 10^5$ in the 5-6 μm range. The stability time of these microspheres is said to be 48 hrs or longer and they permit convenient left heart imaging after intravenous injection. For instance, the sonicated albumin microbubbles when injected into a peripheral vein are capable of transpulmonary passage. This results in echocardiographic opacification of the left ventricle cavity as well as myocardial tissues.

Recently still further improved microballoons for injection ultrasonic echography have been reported in EP-A-324.938 (Widder). In this document there are disclosed high concentrations (more than $10^8$) of air-filled protein-bounded microspheres of less than 10 μm which have life-times of several months or more. Aqueous suspensions of these microballoons are produced by ultrasonic cavitation of solutions of heat denaturable proteins, e.g. human serum albumin, which operation also leads to a degree of foaming of the membrane-forming protein and its subsequent hardening by heat. Other proteins such as hemoglobin and collagen were said to be convenient also in the process of the reference but, in our hands, this was not so.

The high storage stability of the suspensions of microballoons disclosed in EP-A-324.938 enables them to be marketed as such, i.e. with the liquid carrier phase, which is a strong commercial asset since preparation before use is no longer necessary. However, the extreme strength and stability of the membrane material has some drawbacks: for instance, because of their rigidity, the membranes cannot sustain sudden pressure variations to which the microspheres can be subjected, for instance during travel through the blood-stream, these variations of pressure being due to heart pulsations. Thus, under practical ultrasonic tests, a proportion of the microspheres will be ruptured which makes imaging reproducibility awkward. Moreover, it is known that microspheres with flexible walls are more echogenic than corresponding microspheres with rigid walls.

Furthermore, in the case of injections, excessive stability of the material forming the walls of the microspheres will slow down its biodegradation by the organism under test and may result into metabolization problems. Hence it is much preferably to develop pressure sustaining microballoons bounded by a soft and elastic membrane which can temporarily deform under variations of pressure and which is endowed with enhanced echogenicity.

The method of preparation of microballoon suspensions disclosed in EP-A-324.938 involves a two steps sonication of human serum albumin (HSA). In the first step, sonication of a few ml of diluted solution of the protein in a narrow tube is effected with the sonicator head immersed therein; in the second step, sonication is effected with the sonicator head raised above the solution level whereby foaming occurs. Then, the sonicated solution is left aside overnight to decant and the microballoons which gather in the upper layer are collected (float-separation).

This method is rather complicated, lengthy and furthermore adapted to treat protein solutions by small increments (page 4, line 9 of EP-A-324.938). Hence it is apparently not convenient for obtaining larger quantities of mircoballoons required in industrial production.

The method and the composition of the present invention in which foaming of a protein solution and mechanical reduction of the foam bubbles to desired sizes, i.e. by application of shear, occurs sequentially or substantially simultaneously will remedy the foregoing drawbacks (see the claims). It was actually extremely surprising and unexpected that, under certain conditions defined afterwards, the size of the bubbles of an aqueous suspension can be reduced to a desired range of values without significant bubble break and loss of bubble count.

In brief the method consists in converting into a foam an aqueous solution of at least one filmogenic protein, optionally in the presence of a foaming agent, i.e. providing a dispersion of air or gas bubbles in this solution, and thereafter or simultaneously reducing mechanically by attrition or vibration the size of said bubbles (usually at first in a range of 100 μm or more) to a desired value, usually in the 0.5-10 μm range, preferably 4-10 μm, this being achieved by subjecting the foam to high shear, for instance by forcing it though small apertures or passages under mechanical or gas pressure, said passages optionally containing baffle means to increase the shear effect. This can be brought about by means of a homogenizer-emulsifier apparatus or by passing the suspension through a medium, mineral or organic provided with a network of baffled or contorted channels, for instance the material can be a very coarse porous material. Porous mineral media include filtering aids like beds of mineral particles of various sizes or ceramic filters. Organic media include filtering screens well known to those skilled in the art. It should be remarked that during bubble size reduction by passing through baffled channels, the shear effect should be applied incrementally, i.e. the treatment should be applied, in succession, to only small portions of the foam; applying shear at a time to larger portions of foam, i.e. subjecting said portions to too much pressure, may simply lead to temporary bubble size reduction by compression and ultimate restoration of the original bubble size upon pressure release. Evidently, foaming and bubble size reduction can be effected simultaneously when using a suitable homogenizer-emulsifier which can sequentially effect both foaming and size reduction in one operation. We shall see later about the preferred mechanical requirements of this apparatus. Sonic or ultrasonic vibrations might also be effective for bubble size reduction.

The protein solution to be subjected to foaming comprises about 0.1-10% by weight, preferably 0.1-5%, most preferably 0.2-4.9% of a filmogenic protein, i.e. a protein which, when in solution, can contribute to the formation of a film around the bubbles of the foam, such film being sufficiently stable not to collapse under the mechanical action of the homogenizer during bubble size reduction. Proteins that fulfill the foregoing requirements are many and include human serum albumin (HSA), bovine and ovine serum albumins (BSA and OSA), egg albumin, hemoglobin, fibrinogen, globulins, collagen, gelatin, foaming proteins such as hydrolyzed vegetable proteins, hydrolyzed fraction of gluten (Hyfoama), hydrolyzed casein, and the like. When the protein has no or only little intrinsic foaming properties, a foaming agent can optionally added, for instance a physiologically acceptable surfactant. There exists a full range of convenient surfactants from which one may non-exhaustively cite the "Tweens" ®, "Spans" ® and the like.

The solution also contains 40 to 80% by weight of at least one water soluble polyol viscosity enhancer, the amount of which is sufficient to impart thereto a viscosity in the range of 100–600 cP. The viscosity enhancers preferably include polyols with at least 4 hydroxy groups per molecule and with sufficient water solubility to attain the aforementioned concentration values. With lower concentration, the foams obtained are generally too thin, whereas with higher concentration, viscosities are generally too high for efficient homogenization and bubble size reduction. The preferred viscosity enhancers include dextran, polydextrose, glucose, fructose, maltose, corn syrup, sugar syrups (mixtures of sugar monomers and oligomers), partial hydrolyzates of carbohydrates (e.g. starch), synthetic polymers of sugars like glucose and fructose, reduced sugars like sorbitol, mannitol and the like, polyglycerol with at least 4 glycerol units and other similar polyols with sufficient solubility in water. Note that sucrose cannot be used alone because of insufficient viscosity; it can however be used in combination with other more soluble sugars like glucose or fructose. Being given that the viscosity parameter of the solution to be foamed is not sufficient, alone, to impart storage stability to the bubbles, it has been noted that a preferred combination of effective viscosity and enhancer concentration results from using mixtures of carbohydrates of low Mw ($\sim 180$) and average molecular weight ($\sim 300$ to 2000). A full range of starch hydrolyzates fall in this category. Among the polysaccharides one prefers in this invention and which are available commercially, one may cite: Polydextrose N from Pfizer in the U.S. or Great Britain; starch hydrolyzates sold under the names of Mylose ® CN, Mylose ® HM-43-38-250 from Amylum, Belgium, or Flolys ® B-6080S from Roquette, Lestrem, France; high-fructose corn syrups sold under the names of SOS-LU or SIR-O-SWIT ® RE from Amylum.

The homogenizer apparatus used in the present method can have any commercially available head providing sufficient shear force to reduce the size of the bubbles to the desired range of about 0.5–10 $\mu$m. When foaming and bubble size reduction are effected at the same time, i.e. in one operation, a preferred emulsifier head provides simultaneously for high cutting speed, air or gas aspiration, and liquid circulation through apertures the size of which enables to control the bubbles final size. Many emulsifier heads available in the food industry (e.g. POLYTRON) are suitable. A tubular emulsifier head with axial cutter and peripheral longitudinal slits about 1.5 mm wide has given excellent results.

In a typical operation of the invention, a 0.2–1% HSA solution containing 65% by weight of polydextrose (PFIZER), viscosity about 400 cP at 20° C., osmolality about 3 osmol, was foamed and homogenized with a POLYTRON 20 TS emulsifier head for 0.2–5 min at 10–15000 rpm. This resulted into a foam or bubble dispersion of about $10^8$–$10^9$ microbubbles (0.5–5 $\mu$m) per ml which was perfectly stable for several weeks (no significant count change). This dispersion was too viscous to be injected directly for echographic measurements and, after optionally letting it stand at room temperature for a period of time (e.g. 10 to 20 hrs), it was diluted 1:10 to 1:15 with 0.01–0.1% glutaraldehyde solution. After dilution, the concentration was still in the range of $10^7$–$10^8$ but the viscosity was only a few cP and the solution was suitable for injection and echographic measurements. The diluted solution was also stable for several weeks at least.

Alternatively, glutaraldehyde (or any other pharmaceutically acceptable cross-linking agent) can also be used in the starting composition before foaming. Other cross-linking agents include sulfides like cystein, acetyl-cystein, mercaptoethanol, ethanedisulfide; carbodiimides, polyisocyanates; polyacids and anhydrides like maleic anhydrides; and carbohydrate polyesters like esters of sucrose or glucose with lower aliphatic acids or fatty acids. Stabilization can also be achieved by using a 1–10% BSA or HSA solution for dilution. Naturally, if ever desired, stabilization can also be effected by carefully controlled heating for a few seconds to a few minutes in a temperature range of about 60°–120°, preferably in a range of about 65°–80°, the exact value depending on the extent of protein hardening desired.

In the foaming operation, the emulsifier rotor forces the solution to be foamed (or the foam whose bubbles have to be reduced) through the peripheral slits of the tubular head cover and simultaneously aspirates air (or a gas) from the surroundings by forming a central liquid vortex. This provides an intense liquid/air mixing action and a strong shear effect which reduces the size of the bubbles of the foam. Naturally air can be replaced by any physiologically acceptable gas, e.g. $N_2$, Ar and other noble gases, $N_2O$, hydrocarbon vapors, $CH_4$ and the like.

If the solution is foamed first and the size of the bubbles of the foam reduced subsequently as indicated, the foaming operation can be carried out using any conventional blender or whipping equipment. For instance, one apparatus embodiment comprises a pyrex reactor with bottom discharge provided with a cooling mantle for temperature control, a blade agitator for rotating the composition before and during foaming, and a cutter-crusher head to provide shear and effect foaming, homogenization and bubble size reduction. Sterilization of the ingredients can be effected directly the reactor. Usually, operating with the foregoing reactor preferably involves the following steps:

1) Placing the sugar solution (for instance the solution of polydextrose or of corn-syrup) into the reactor.
2) Starting the blade mixer.
3) Optionally sterilizing the solution by heat.
4) Introducing the albumin solution (sterilized beforehand). 5) Starting the foaming and bubble size-reducing head. Carefully controlling the temperature below protein denaturation temperature by means of the cooling mantle.
6) Adding a very small amount of cross-linker.
7) Cooling with slow stirring.
8) Allowing to rest for a period of time at ambient temperature.
9) Discharging the suspension through the bottom opening.

During foaming the operating temperature is ambient at the start and, in view of the heat developed by shear in homogenization, it is preferably controlled, particularly at the bubble reduction stage, not to exceed values which might cause protein denaturation and excessive hardening of the microsphere walls. Normally, it is preferred to keep the temperature below 50°, preferably below 35°–40° C. as, if the temperature were to rise to levels where denaturation occurs, the yields would be much affected. The homogenization time involved can be from about a fraction of a minute to several minutes, i.e. 5–10 minutes, this being dependent on the amount of material used. It should be remarked that although too high temperature due to shear energy may be detrimental during foaming or bubble size reduction, the terminated suspension of microbubbles can be heated, if desired, to temperatures above 50° C. without detrimental effects. Actually, heating the terminated bubble suspension, either before or after dilution, will effect progressive hardening of the filmogenic proteins making the bubble walls, this changing somewhat the bubble properties and contributing to their stability with time under storage. Practically, heating for a few seconds to a few minutes at, say, 60°-120° C. will cause the protein to harden by denaturation into useful range of properties.

It has additionally be found that the diluted, ready-to-be-injected solution can be dessicated to a dry friable solid by the conventional techniques of freeze-drying. This solid can be stored for an indefinite length of time under dry conditions without alteration and the original injectable suspension can be regenerated integrally (no loss of bubbles) by simply adding thereto a corresponding amount of water or a physiologically acceptable liquid designed for injections. Regarding the water used for providing the injectable microsphere suspensions, it has been noted that fully degassed types (like distilled water) should be avoided for lack of bubble stability. The preferred types of waters to effect foam dilution should be sterile but aerated; ordinary tap water or natural mineral drinking waters are well suitable. It appears that a small proportion of dissolved minerals (which is normal in the water available from domestic lines) aids in stabilizing the bubbles in the suspensions under storage.

The following examples illustrate the invention in detail. In the examples, viscosity values were measured at 25° C. with a HAAKE spinning viscometer, head ME-30 (1-1000 cP depending on spinning rate); the bubble concentrations were measured with a Hematocytometer comprising a grated microscope slide, the counting areas being $1 \times 1$ mm, 100 $\mu$m thick (0.1 $\mu$l). The solution to be counted were appropriately diluted beforehand to allow for about 50-100 bubbles in the counting area. Alternatively, a conventional Coulter Counter was used.

The bubble sizes and size distribution were measured with a MALVERN Mastersizer ® apparatus; this is based on directing a calibrated beam of monochromatic light (laser beam) to a cell for holding the suspension to be examined and measuring the parameters of the diffraction patterns.

EXAMPLE 1

Bovine Serum Albumin was obtained as the usual commercial 5% solution and it was freeze-dried to give a free-flowing pale yellow powder.

The solid BSA was dissolved in water to give a 20% by weight solution (stock solution).

A composition with 65% by weight of viscosant was made by mixing together 300 g of a 70% by weight aqueous polydextrose solution (PFIZER), 18 g of water, 6 g of the foregoing stock solution and 0.3 g of glutaraldehyde. The viscosity at 25° C. was 460 cP. A Polytron emulsion-head with 1.5 mm wide slits was immersed in the composition and foaming plus emulsification was carried out for about ½-1 minute at room temperature (20°-25° C.) without cooling. The emulsification energy raised the temperature to about 30°-35° C. This resulted in a microbubble suspension containing about $10^9$ bubbles/ml (Coulter Counter), most of the bubbles being in the 1.5-2 $\mu$m range (Malvern). The viscosity was substantially the same as that of the starting solution, therefore dilution with water (1:13) or saline was carried out to give an easily injectable liquid with about $7.7 \times 10^4$ bubbles/cubic mm (viscosity about 5-10 cP).

Echogenic measurements were performed with a pulse-echo system consisting of a plexiglas specimen holder (diameter 30 mm) with a 20 $\mu$m thick Mylar acoustic window, a transducer holder immersed in a constant temperature water bath, a pulser-receiver (Accutron M3010JS) with an external preamplifier with a fixed gain of 40 dB and an internal amplifier with gain adjustable from $-40$ to $+40$ dB and interchangeable 13 mm unfocused transducers. A 10 MHz low-pass filter was inserted in the receiving part to improve the signal to noise ratio. The A/D board in the IBM PC was a Sonotek STR 832. Measurements were carried out at 7.5 MHz.

Echogenic values in the range of 0.02 were obtained with the aforementioned dilution. After further dilution in a ratio of about $10^{-2}$ to $10^{-3}$, echogenic values in the range of 0.04-0.06 were observed.

Identical results were obtained if in the foregoing Example the bovine serum albumin (BSA) was replaced by an identic amount of human serum albumin (HSA).

EXAMPLE 2

Three hundred gram of modified corn syrup (SIR-O-SWIT LU consisting mainly of glucose, fructose, maltose and minor amounts of other sugars) from AMYLUM Company, Belgium, with 70% by weight sugars (density=about 1.45) were mixed with 6 g of aqueous 20% HSA and 18 g of water. The 25° C. viscosity was about 420 cP. The solution was foamed and emulsified under an atmosphere of nitrogen for 3 min with a POLYTRON emulsifier head, the temperature being kept below 40° C. to prevent hardening and water-insolubilization of the protein by denaturation.

After homogenization, the suspension was diluted to about 1/10 with water containing 0.07% of formaldehyde and counted for bubble concentration (found about $5 \times 10^7$/ml of diluted suspension). The bubble size distribution was 80% in the 0.5-3 $\mu$m range (viscosity a few cP). Both the concentrated and diluted bubble suspensions were stable for at least 4 weeks with no significant bubble count change.

EXAMPLE 3

The procedure of the previous Examples was repeated by using 20% b.w. aqueous HSA as the protein and 42% b.w. Dextrose as the viscosity enhancer ingredient (viscosity 518 cP at 25° C.). Foaming and homogenization was carried out for 1 min at temperature below 35° C. The microbubble suspension (about $10^9$/ml) was stable for at least 15 days. After dilution (1/10) with 5% HSA solution, its viscosity dropped to about 15-20 cP and was suitable for injection and echographic investigations. It was also stable for several hours in diluted form. Stability with time was further increased after heating for about 2 min at 70°-75° C.

EXAMPLE 4

The procedure of Example 1 was repeated but replacing the BSA by other proteins. The other parameters were like in Example 1. The Table I below reports the results in terms of microbubble concentrations of the undiluted suspensions. After dilution with either saline (0.9% aqueous NaCl) or other pharmaceutically acceptable aqueous diluents and stabilizers, injectable suspensions of microbubbles suitable for echogenic investigations were obtained.

TABLE I

|  | Proteins | | |
| --- | --- | --- | --- |
|  | Hemoglobin* | Hyfoama 77** | Bovine Plasma*** |
| Concentration ×10[7] | 67 | 12 | 4 |
| Stability | >24 hrs | >1 week | — |

*From FLUKA AG, Buchs, Switzerland
**Partial hydrolysate of gluten from QUEST INT., Zwijndrechd, Holland
***From Herman LAUE AG, CH-6055 Alpnach, Switzerland.

EXAMPLE 5

To the 1 liter reactor (detailed previously) were added in turn 30 ml of water and 36 g of 5% aqueous human serum albumin (HSA). The agitator was started (25 rpm) and the temperature was controlled to 20° C. Then the Polytron ® head (3 mm slits) was started at 11,000 rpm while continuing the slow agitation and the reaction was allowed to proceed for 25 min while the temperature was controlled not to exceed 40° C. Then, 1.29 ml of 50% aqueous glutaraldehyde were added and homogenization was continued for a few minutes whereas the temperature was kept under 45° C. The cutter head was stopped and the mixture was cooled to room temperature in about 10 min. The bubble suspension was allowed to rest in the reactor for about 12 hrs after which it was drained through the bottom (the froth at the reactor top was discarded) and stored in glass containers. The bubble concentration was in the range $10^8$–$10^9$/ml, and more than 90% of the bubbles were in the size range 1–10 μm.

A 1 ml sample of the concentrated bubble suspension was diluted with 12 ml of tap water and quickly frozen at −20° to −40° C. in a cold enclosure; then it was subjected to reduced pressure ($10^{-3}$–$10^{-4}$ mm) while allowing it to slowly come back to room temperature (the condenser placed between the vacuum flask and the pump was kept at about −40° C.). After complete evaporation, there remained a thin and frangible solid mass which could be stored indefinitely under dry conditions (hygroscopicity) without appreciable changes. After a long storage period (several weeks), the solid was taken with 12 ml of water which regenerated a bubble suspension with the original bubble count (about $10^7$/ml).

EXAMPLE 6

A series of preparations (labeled 103 to 127) were carried out according to the general procedure outlined in Example 5, but progressively modifying some of the operating parameters. The operating conditions and the results are summarized in the Table II provided in annex. In the Table, the successive column headings refer in the order to the following parameters: Sample number; Kind of sugar solution for viscosity build-up; weight % of dissolved sugar (counted as dry); pH of the mixture subjected to treatment; weight % of albumin used therein; weight % of cross-linker. The next four columns need no further comments after which the remaining columns (starting with the 11th) refer to the following parameters: width of the slots in the Polytron ® cutter head; The temperature (and optionally the time) at which the preparation was allowed to rest before draining; the concentration of bubbles in the concentrated suspension as ascertained with the Hematocytometer; the light absorption of a sample of diluted suspension (dilution adjusted to 10% by weight of solids in water); the "volume" average size of the microbubbles: the "number" average size of said bubbles (both measured with the Mastersizer ®): and finally the "dispersivity" parameter, a figure of merit; obviously, the smaller the figure, the narrower the size distribution.

TABLE II

| Sample name | Fluid vector | Dry extract (%) | pH | % Albumine | % Glutar-aldehyde | Starting temp. (°C.) | Final temp. (°C.) | Emulsion time (min) | Homogenizer speed (rpm) |
| --- | --- | --- | --- | --- | --- | --- | --- | --- | --- |
| 103a | Glucose syrup | 72.5 | 4.7 | 0.26 | 0.144 | 22.5 | 40.0 | 8 | 11000 |
| 103b | SOS RE | 72.5 | 4 | 0.26 | 0.144 | 22.0 | 40.0 | 11 | 11000 |
| 104a | SOS RE | 72.5 | 6.6 | 0.26 | 0.144 | 22.0 | 40.0 | 12 | 11000 |
| 104b | SOS RE | 70 | 4 | 0.26 | 0.144 | 22.0 | 40.0 | 13 | 11000 |
| 105a | SOS RE | 70 | 4 | 0.26 | 0.144 | 22.0 | 40.0 | 26 | 5000 |
| 105b | Glucose syrup | 65.6 | 4.7 | 0.26 | 0.144 | 22.0 | 43.0 | 10 | 11000 |
| 106a | SOS RE | 65 | 4 | 0.26 | 0.144 | 22.0 | 40.0 | 8 + heating | 10000 |
| 106b | SOS RE | 60 | 4 | 0.26 | 0.144 | 22.0 | 40.0 | 8 + heating | 10000 |
| 107a | SOS RE | 65.1 | 4 | 0.2 | 0.144 | 30.0 | 40.0 | 10 + heating | 10000 |
| 108a | SOS RE | 70 | 4 | 0.2 | 0.144 | 40.0 | 45.5 | 5 + heating | 10000 |
| 108b | Polydextrose | 67.3 | 6 | 0.2 | 0.144 | 40.0 | 46.0 | 5 + heating | 10000 |
| 109a | Polydextrose | 65.1 | 6 | 0.2 | 0.144 | 40.0 | 45.3 | 5 + heating | 10000 |
| 109b | Polydextrose | 67.3 | 6 | 0.2 | 0.144 | 25.0 | 46.0 | 14 | 10000 |
| 110a | Glucose syrup | 75 | 4.7 | 0.2 | 0.144 | 25.0 | 46.0 | 15 | 10000 |
| 110: | Dextrose:Glucose syrup (80:20) | 72.6 | 6.1 | 0.2 | 0.144 | 25.0 | 44.0 | 30 | 10000 |
| 111a | Polydextrose | 67.3 | 6 | 0.2 | 0.144 | 25.0 | 45.0 | 16 | 10000 |
| 111b | Polydextrose | 67.3 | 6 | 0.2 | 0.144 | 25.0 | 45.0 | 14 | 10000 |
| 112a | Mylose HM4338250 | 67 | 5 | 0.2 | 0.144 | 30.0 | 45.0 | 10 | 10000 |
| 112b | Mylose HM4338250 | 67 | 5 | 0.2 | 0.144 | 30.0 | 45.0 | 14 | 10000 |
| 113a | Mylose HM4338250 | 67 | 5 | 0.2 | 0.144 | 20.0 | 45.0 | 13 | 11000 |
| 113b | Mylose HM4338250 | 67 | 5 | 0.2 | 0.144 | 15.0 | 45.0 | 21 | 12000 |
| 114a | Mylose HM4338250 | 70 | 5 | 0.2 | 0.144 | 15.0 | 45.0 | 17 | 12000 |
| 114b | Dextrose + pectine 0.38% | 65 | 3.9 | 0.2 | 0.144 | 20.0 | 45.0 | 35 | 12000 |
| 116a | Glucose syrup | 70.5 | 4.7 | 0.2 | 0.144 | 20.0 | 45.0 | 19 | 11000 |
| 116b | Glucose syrup:Polydextrose | 70.3 | 5.5 | 0.2 | 0.144 | 20.0 | 45.0 | 14 | 11000 |
| 117a | Glucose syrup | 75 | 4.7 | 0.2 | 0.144 | 20.0 | 45.0 | 13 | 11000 |
| 119c | Invert sugar | 70.6 | 5.4 | 0.2 | 0.144 | 20.0 | 45.0 | 24 | 11000 |
| 121c | Invert sugar | 75.1 | 5.4 | 0.2 | 0.144 | 20.0 | 45.0 | 14 | 11000 |
| 122e | Mylose HM4338250 with 1% gelatine | 67 | 5 | 0.2 | 0.144 | 30.0 | 45.0 | 10 | 10000 |
| 122c | Mylose HM4338250 with 2% gelatine | 67 | 5 | 0.2 | 0.144 | 30.0 | 45.0 | 10 | 10000 |
| 122d | Mylose HM4338250 with 2% gelatine | 67 | 5 | 0.2 | 0.144 | 30.0 | 45.0 | 10 | 10000 |

TABLE II-continued

| Sample name | Fluid vector | Slot size (mm) | Cooling temp. (°C.) | Concentration (Particles/ml) | Obscuration at 10% | sv (μm) | sn (μm) | Plzsv/ sn | Sample name |
|---|---|---|---|---|---|---|---|---|---|
| 124b | Mylose CN | 70 | 4.6 | 0.2 | 0.144 | 25.0 | 45.0 | 21 | 11000 |
| 125a | Mylose CN | 75 | 4.6 | 0.2 | 0.144 | 25.0 | 45.0 | 13 | 11000 |
| 125b | Mylose CN | 73 | 4.6 | 0.2 | none | 25.0 | 45.0 | 15 | 11000 |
| 126a | Invert sugar | 70.6 | 4.4 | 0.2 | 0.144 | 20.0 | 45.0 | 22 | 11000 |
| 127a | Invert sugar | 70.6 | 5.4 | 0.2 | none | 20.0 | 45.0 | 22 | 11000 |
| 103a | Glucose syrup | 1.5 | 23 | 2.00E+09 | 0.126 | 1.71 | 0.86 | 1.99 | 103a |
| 103b | SOS RE | 1.5 | 23 | 2.00E+09 | 0.293 | 1.87 | 0.79 | 2.37 | 103b |
| 104a | SOS RE | 1.5 | 23 | 4.50E+08 | 0.021 | 1.15 | 0.7 | 1.64 | 104a |
| 104b | SOS RE | 1.5 | 23 | 2.10E+09 | 0.057 | 1.2 | 0.76 | 1.58 | 104b |
| 105a | SOS RE | 3.0 | 23 | 6.70E+08 | 0.022 | 4.16 | 0.97 | 4.29 | 105a |
| 105b | Glucose syrup | 1.5 | 23 | 100E+09 | 0.062 | 5.82 | 1.11 | 5.24 | 105b |
| 106a | SOS RE | 1.5 | 41 | 1.50E+09 | 0.071 | 3.51 | 0.87 | 4.03 | 106a |
| 106b | SOS RE | 1.5 | 3 h at 43° C. | 5.00E+09 | 0.005 | 6.28 | 1.06 | 5.92 | 106b |
| 107a | SOS RE | 1.5 | 3 h at 43° C. | | | | | | 107a |
| 108a | SOS RE | 1.5 | 23 | | | | | | 108a |
| 108b | Polydextrose | 1.5 | 24 | 9.24E+08 | 0.076 | 2.58 | 0.97 | 2.66 | 108b |
| 109a | Polydextrose | 1.5 | 25 | 1.00E+09 | 0.036 | 3.56 | 1 | 3.56 | 109a |
| 109b | Polydextrose | 1.5 | 30 | 1.60E+09 | 0.095 | 2.47 | 0.81 | 3.05 | 109b |
| 110a | Glucose syrup | 1.5 | 27 | 1.30E+09 | 0.067 | 2.74 | 0.82 | 3.34 | 110a |
| 110b | Dextrose:Glucose syrup (80:20) | 1.5 | 30 | * | * | * | * | * | 110b |
| 111a | Polydextrose | 1.5 | 25 | 1.56E+09 | 0.285 | 1.49 | 0.93 | 1.6 | 111a |
| 111b | Polydextrose | 1.5 | 20 | 1.56E+09 | 0.408 | 1.37 | 0.91 | 1.51 | 111b |
| 112a | Mylose HM4338250 | 3.0 | 25 | 4.10E+08 | 0.031 | 2.57 | 1.03 | 2.5 | 112a |
| 112b | Mylose HM4338250 | 1.5 | 25 | 1.00E+09 | 0.114 | 1.53 | 0.95 | 1.61 | 112b |
| 113a | Mylose HM4338250 | 3.0 | 25 | 4.16E+08 | 0.021 | 2.59 | 1.2 | 2.16 | 113a |
| 113b | Mylose HM4338250 | 3.0 | 25 | 7.80E+08 | 0.025 | 2.36 | 1.16 | 2.03 | 113b |
| 114a | Mylose HM4338250 | 3.0 | 25 | 1.00E+09 | 0.026 | 2.89 | 0.88 | 3.28 | 114a |
| 114b | Dextrose + pectine 0.38% | 3.0 | 25 | * | * | * | * | * | 114b |
| 116a | Glucose syrup | 3.0 | 25 | 9.36E+08 | 0.068 | 1.69 | 0.88 | 1.92 | 116a |
| 116b | Glucose syrup:Polydextrose | 3.0 | 25 | 8.30E+08 | 0.027 | 3.63 | 0.82 | 4.43 | 116b |
| 117a | Glucose syrup | 3.0 | 25 | 9.36E+08 | 0.039 | 2.83 | 0.76 | 3.72 | 117a |
| 119c | Invert sugar | 3.0 | 25 | 7.80E+08 | 0.022 | 3.05 | 1.65 | 1.85 | 119c |
| 121c | Invert sugar | 3.0 | 25 | 7.80E+08 | 0.006 | 6.95 | 1.2 | 5.79 | 121c |
| 122e | Mylose HM4338250 with 1% gelatine | 3.0 | 25 | 1.66E+08 | 0.127 | 1.6 | 0.91 | 2.5 | 122e |
| 122c | Mylose HM4338250 with 2% gelatine | 3.0 | 25 | | 0.078 | 1.6 | 0.94 | 2.5 | 122c |
| 122d | Mylose HM4338250 with 2% gelatine | 3.0 | 25 | 8.70E+07 | 0.099 | 1.62 | 0.92 | 2.5 | 122d |
| 124b | Mylose CN | 3.0 | 25 | 8.00E+08 | 0.268 | 2.57 | 0.66 | 3.89 | 124b |
| 125a | Mylose CN | 3.0 | 25 | 7.80E+08 | 0.309 | 4.82 | 0.73 | 6.60 | 125a |
| 125b | Mylose CN | 3.0 | 25 | 7.00E+08 | 0.04 | 8.52 | 0.47 | 18.13 | 125b |
| 126a | Invert sugar | 3.0 | 25 | 8.30E+08 | 0.155 | 6.88 | 2.05 | 3.36 | 126a |
| 127a | Invert sugar | 3.0 | 25 | 8.30E+08 | 0.01 | 48.8 | 6.4 | 7.63 | 127a |

*crystallization

We claim:

1. A method for preparing stable aqueous suspensions of air or gas filled microbubbles suitable for ultrasonic applications in living organisms, said method comprising the steps of:
   a) converting a viscous aqueous solution of a filmogenic protein into a foam of air or gas filled bubbles by whipping with air or a pharmaceutically acceptable gas to produce microbubbles bound by a membrane of said protein, and
   b) subjecting, simultaneously or subsequently, the foaming solution to high shear by forcing it through narrow openings or channels for a time sufficient to reduce the size of the bubbles in the foam to values in a range of about 0.5–10 μm suitable for injection.

2. The method of claim 1, wherein said openings or channels contain baffling means.

3. The method of claim 1, in which the foam is subjected to high shear in a homogenizer and emulsifier apparatus comprising a tubular head with parallel axially oriented slits at the periphery and an axially rotating cutter in the center the action of which causes air from the surroundings to be admixed with the liquid and the air-liquid mixture to be forced radially through the slits, thus subjecting the foam to a high shear effect.

4. The method of claim 3, in which the temperature is kept below 50° C. during foaming and bubble size reduction to avoid protein denaturation by the heat developed by the homogenizer-emulsifier apparatus.

5. The method of claim 1, in which the resulting suspension has a concentration of microbubbles in the range of $10^8$–$10^9$/ml.

6. The method of claim 1, in which the resulting suspension is further diluted with water or a physiologically acceptable liquid to decrease the viscosity to a few cP so as to make it directly injectable into the bloodstream of living bodies.

7. The method of claim 6, in which the diluted solution is freeze-dried into a solid which can be kept unchanged for an indefinite period in dryness and which will regenerate the suspension of microbubbles upon admixing with a corresponding quantity of water or a physiologically acceptable liquid suitable for injections.

8. The method of claim 6, in which the diluting liquid comprises a stabilizer to increase the storage stability of the diluted suspension.

9. The method of claim 8, wherein the stabilizer is an organic aldehyde.

10. The method of claim 6, which comprises heating the diluted solution to temperatures between 60° and 120° C. for a few seconds to a few minutes to effect hardening of the membrane protein by denaturation.

11. The method of claim 1, in which the foam is subjected to high shear by forcing it through a mineral or organic material with a plurality of baffled channels providing attrition effects on the bubbles.

12. The method of claim 5, in which the resulting suspension is further heated at 60°–120° C. for a few seconds to a few minutes to modify the properties of the bubble bounding protein by progressive denaturation.

13. An aqueous composition to be converted by the method of claim 1 to a suspension of microbubbles suitable for ultrasonic echography, comprising, in solution, 0.1–5% by weight of a filmogenic protein and 40–80% by weight of a water-soluble polyol viscosity enhancer to raise the ambient temperature viscosity to about 100–600 cP.

14. The composition of claim 13, comprising surfactants as foam enhancers and cross-linking agents for increasing stability of the foam.

15. The composition of claim 13, in which the polyol viscosity enhancer has at least four OH groups per molecule.

16. The composition of claim 15, in which the viscosity enhancer is selected from the group consisting of polyalcohols, mono-, poly- and oligosaccharides and mixtures thereof.

17. The composition of claim 16, in which the viscosity enhancer is selected from the group consisting of glucose, fructose, mannose, dextrose, dextran, polydextrose, sugar syrups, corn syrup, polyglycerol with at least four glycerol units, and mixtures thereof.

18. The composition of claim 13, in which a stabilizing agent is present.

19. The composition of claim 18, in which the stabilizing agent is formaldehyde or glutaraldehyde.

20. The suspension of microbubbles which results from carrying out the method of claim 1, said suspension being stable for at least four weeks.

21. The suspension of claim 20, in which stability is further increased by heating to 60°–120° C. for a few seconds to a few minutes to effect hardening of the filmogenic protein.

22. A method of conducting an echographic investigation of a living body, said method comprising the steps of:
 a) diluting a suspension of air or gas filled microbubbles produced according to the method of claim 19 with a physiologically acceptable liquid to obtain a suspension with a viscosity of about 2–30 cP;
 b) injecting the diluted suspension obtained into the blood-stream of said body, and
 c) obtaining an echographic response generated by said body.

* * * * *